(12) United States Patent  (10) Patent No.: US 9,212,259 B2
Kim et al.  (45) Date of Patent: Dec. 15, 2015

(54) NITRIC OXIDE DELIVERY SYSTEM USING THERMOSENSITIVE SYNTHETIC POLYMERS

(75) Inventors: Won Jong Kim, Gyeongsangbuk-do (KR); Yanggy Lee, Gyeongsangnam-do (KR); Kwideok Park, Seoul (KR); Jihoon Kim, Gyeongsangbuk-do (KR); Dong Keun Han, Seoul (KR)

(73) Assignee: POSTECH ACADEMY-INDUSTRY FOUNDATION, Kyungsangbuk-Do (KR)

( * ) Notice: Subject to any disclaimer, the term of this patent is extended or adjusted under 35 U.S.C. 154(b) by 142 days.

(21) Appl. No.: 13/877,384

(22) PCT Filed: Oct. 4, 2011

(86) PCT No.: PCT/KR2011/007316
§ 371 (c)(1),
(2), (4) Date: Apr. 2, 2013

(87) PCT Pub. No.: WO2012/046994
PCT Pub. Date: Apr. 12, 2012

(65) Prior Publication Data
US 2013/0189340 A1    Jul. 25, 2013

(30) Foreign Application Priority Data
Oct. 4, 2010   (KR) .................. 10-2010-0096520

(51) Int. Cl.
*A61K 47/34* (2006.01)
*A61L 27/34* (2006.01)
(Continued)

(52) U.S. Cl.
CPC ............... *C08G 73/024* (2013.01); *A61L 27/34* (2013.01); *A61L 27/54* (2013.01);
(Continued)

(58) Field of Classification Search
CPC .. A61K 47/34; A61L 2300/114; A61L 27/34; A61L 27/54; C08G 63/6852; C08G 73/0206; C08G 73/024; C08L 71/02
See application file for complete search history.

(56) References Cited

U.S. PATENT DOCUMENTS

| 5,405,166 A | 4/1995 | Rogerson |
| 5,931,497 A | 8/1999 | Fischer |
| 2007/0286840 A1* | 12/2007 | Arnold et al. .............. 424/78.35 |

FOREIGN PATENT DOCUMENTS

| CN | 1861041 A | 11/2006 |
| CN | 101287505 A | 10/2008 |

(Continued)

OTHER PUBLICATIONS

Abdellatif et al. (Bioorganic & Medicinal Chemistry Letters 2009, 19:3014-4018) and Hrabie et al. (Chemical Reviews 2002;102:1135-1154).*

(Continued)

*Primary Examiner* — Ernst V Arnold
(74) *Attorney, Agent, or Firm* — Fitch Even Tabin & Flannery LLP (57) ABSTRACT

A donor capable of controlled release of nitric monoxide and a prosthetic implant whose surface is coated with this donor are disclosed. The donor comprises a main chain of an organic polymer and a side chain that is covalently linked to the main chain and has a diazeniumdiolate functional group. The donor for controlled release of nitric monoxide exists in a fluid state such as liquid at room temperature and undergoes a sol-to-gel phase transition at a physiological pH as the temperature increases above the critical temperature. The critical temperature of the phase transition is in the range of 25 to 35° C., and the gel is a hydrogel without chemical cross-links.

7 Claims, 7 Drawing Sheets

(51) Int. Cl.
| | |
|---|---|
| C08L 71/02 | (2006.01) |
| C08G 73/02 | (2006.01) |
| A61L 27/54 | (2006.01) |
| C08G 63/685 | (2006.01) |

(52) U.S. Cl.
CPC ....... *C08G 63/6852* (2013.01); *C08G 73/0206* (2013.01); *C08L 71/02* (2013.01); *A61K 47/34* (2013.01); *A61L 2300/114* (2013.01)

(56) References Cited

FOREIGN PATENT DOCUMENTS

| | | |
|---|---|---|
| JP | H07-329694 A | 12/1995 |
| JP | H08-507989 A | 8/1996 |
| JP | H10-53084 A | 2/1998 |
| JP | 2007-050848 A | 3/2007 |
| JP | 2010-508925 A | 3/2010 |
| JP | 2010-155566 A | 7/2010 |
| JP | 2010-535121 A | 11/2010 |
| JP | 2012-046072 A | 3/2012 |
| JP | 2013-23076 A | 2/2013 |
| KR | 10-0474528 B1 | 3/2005 |
| KR | 10-2008-0003320 A | 1/2008 |
| KR | 10-2008-0017850 A | 2/2008 |
| KR | 10-2008-0037677 A | 4/2008 |
| WO | 2006/100156 A2 | 9/2006 |
| WO | 2008/055719 A2 | 5/2008 |
| WO | 2008/122346 A1 | 10/2008 |

OTHER PUBLICATIONS

Hrabie et al. (Chemical Reviews 2002;102:1135-1154).*
Office Action issued in corresponding Chinese Application No. 201180048542.0 dated Mar. 4, 2014 and English translation of same (11 pages).
H. H. H. W. Schmidt and M. Kelm, "Determination of Nitrite and Nitrate by the Griess Reaction" in "Methods in Nitric Oxide Research" edited by Martin Feelish and Jonathan S. Stamler, published by John Wiley & Sons, 1996, pp. 491-497 (6 pages).
International Search Report and Written Opinion from International Bureau of WIPO for corresponding International Application No. PCT/KR2011/007316 dated Apr. 4, 2012 (7 pages).
Notice of Allowance issued in counterpart Korean Application No. 10-2010-0096520 dated Mar. 28, 2013 (5 pages) and an English translation of the same (1 page).

* cited by examiner

NITRIC OXIDE DELIVERY SYSTEM USING THERMOSENSITIVE SYNTHETIC POLYMERS

CROSS-REFERENCE TO RELATED APPLICATIONS

This application is a National Phase Patent Application of International Patent Application Number PCT/KR2011/007316, filed Oct. 4, 2011, which claims priority of Korean Patent Application Number 10-2010-0096520, filed Oct. 4, 2010, which is hereby incorporated herein by reference in their entirety.

TECHNICAL FIELD

The present invention relates to a nitric oxide donor, and more particularly, to a thermosensitive nitric oxide-releasing polymer capable of controlled release of nitric monoxide.

BACKGROUND ART

The present invention is a result of conducting the promising and pioneering research project led by the Korean Ministry of Education, Science and Technology, which had been hosted by Korea Institute of Science and Technology by 28 Feb. 2011 from 1 Apr. 2010, entitled "Development of a nitric oxide-releasing, blood-compatible stent" (Assignment No.: 20100002175).

Nitric (mon)oxide (NO) is a biomodulator exhibiting potency in a variety of fields. In 1992, NO was nominated as the "molecule of the year" by the American journal Science, and was the main research subject of the 1998 Nobel Prize in Physiology and Medicine. NO acts as a signaling molecule in the human body and is also formed as a product from an immune reaction. Physiological effects of NO encompass expansion of blood vessels, neurotransmission, regulation of the hair cycle, generation of reactive nitrogen-containing intermediates, regulation of penile erection, antibacterial effects, antivirus effects, and wound healing.

Among such physiological effects of NO, the expansion of blood vessels has received much attention. In vascular endothelial cells, NO transmits a signal for relaxation to the surrounding smooth muscle cells, whereby blood vessels expand and more blood flows therethrough. In addition, NO prevents contraction and growth of vascular smooth muscles and prevents aggregation of platelets in endothelia and adhesion of white blood cells to endothelia, contributing to maintaining homeostasis of blood vessels.

An angioplasty accompanying stent insertion is performed on patients with blocked coronary blood vessels due to accumulation of fat mass therein. In an angioplasty procedure, a small balloon is inserted into a blood vessel and then inflated, thereby forcing the fat mass tightly towards the walls of the blood vessel, and, as a result, the blood vessel is widened. In this regard, a tube-shaped mesh scaffold called a stent is inserted into the blood vessel, thereby forcibly maintaining the width of the blood vessel. In some cases, the blood vessel returns back to its narrow width, necessitating another angioplasty operation. Therefore, if one can find means to controllably release medications such as NO capable of preventing cell growth and inflammation from a stent, this may significantly contribute to a successful angioplasty procedure.

There are various compounds that are capable of releasing NO from the surface of an artificial implant such as a stent. Examples of the compounds include organic nitrates, esters, iron-nitrosyl complexes, sydnonimine, C-nitroso compounds, and S-nitrosothiols (R—S—NO). In particular, research into S-nitrosothiols has been actively conducted. Unfortunately, there has been cases where implants harboring these compounds failed to release NO into the human body and the rate of releasing NO is affected by the concentration of copper ions ($Cu^+$). In addition, S-nitrosothiols are not stable themselves and thus difficult to obtain in a pure form.

Therefore, research into a novel material capable of more efficiently releasing NO and a method of more efficiently releasing NO has recently been actively conducted. Also, if the release of NO is more efficiently performed, an artificial implant needs to include a member capable for adjusting a rate of release occurring on a surface of the artificial implant.

A high concentration of NO is toxic, and since it is a vasodilator, an excess amount of NO in the human body can cause a total collapse of the circulatory system. Thus, a significant improvement in the performance of prosthetic implants can be achieved by developing a delivery system for releasing NO, which releases or, when necessary, suppresses or delays the release of an appropriate concentration of NO at an appropriate rate in response to signals from the surroundings, the release characteristics of which being unaffected by unwanted noise from the surroundings. When conventional NO delivery systems are used, an excess amount of NO is released at an early stage and it is thus difficult to achieve sustained release of NO.

SUMMARY OF THE INVENTION

The present invention provides a polymeric nitric monoxide donor capable of delayed or controlled release of nitric monoxide from a prosthetic implant within the body.

The present invention also provides a prosthetic implant comprising the polymeric nitric monoxide donor on its surface.

According to an aspect of the present invention, there is provided a donor for controlled release of nitric oxide. The donor is a polymer including a main chain of an organic polymer and a side chain that is covalently linked to the main chain and has a diazeniumdiolate functional group. The donor exists in a fluid state such as a liquid at room temperature and undergoes a sol to gel phase transition at in vivo pH as the temperature increases above a critical temperature. The critical temperature of the phase transition is in a range of 25 to 35° C., and the gel is a hydrogel not including chemical cross-links.

To obtain such a hydrogel, the carbon backbone of the main chain of the donor may be a block copolymer selected from the group consisting of an ethylene glycol/propylene glycol copolymer, a lactate/glycolate copolymer, a lactate/ethylene glycol copolymer, a lactate-glycolate-ethylene glycol copolymer, a lactate-glycolate-propylene glycol-ethylene glycol copolymer, an ε-caprolactone/ethylene glycol copolymer, a 3-hydroxybutyrate/propylene glycol copolymer, a propylene fumarate/ethylene glycol copolymer, an organophosphagen/ethylene glycol copolymer, and a polypeptide-based block copolymer.

The side chain of the donor may be a polymer selected from the group consisting of secondary amine-containing polymers such as polyethyleneimines, polypropyleneimines, and secondary amine-containing polypeptides, and biopolymers such as chitosan.

The donor may further include a pharmaceutically active material in the hydrogel. The pharmaceutically active material may be selected from the group consisting of a vascular endothelial growth factor (VEGF), an anti-inflammatory agent, vitamin C, acetylsalicylate, a cholesterol-lowering drug, a thrombolytic agent, an antithrombotic agent, heparin, anticancer drugs and oligonucleotides with anti-proliferative activity.

The pharmaceutically active material may not be directly linked covalently to the donor, but may be dispersed in the hydrogel, or may be a conjugate that is covalently linked to oxygen atoms of the diazeniumdiolate functional group of the side chain of the donor.

According to another aspect of the present invention, there is provided a prosthetic implant including the donor coated on its surface.

According to one or more embodiments of the present invention, there is provided a donor for controlled release of nitric oxide, in the form of a thermosensitive hydrogel. The donor is capable of stably and biocompatibly providing nitric monoxide in vivo over a long period of time. The donor and a prosthetic implant including the donor coated on its surface are expected to be widely used in medical and health applications, for example, treatment of ischaemic disorders such as arteriosclerosis, regulation of penile erection, antibacteria and antivirus fields, and wound healing.

DETAILED DESCRIPTION OF THE PREFERRED EMBODIMENTS

The present invention will now be described in detail.

According to an embodiment of the present invention, there is provided a donor for controlled release of nitric monoxide (NO) which is coated on a surface of an artificial device to be located in a human body to form a thermosensitive hydrogel, whereby the controlled release of NO is performed.

According to another embodiment of the present invention, there is provided a prosthetic implant with the donor on its surface.

According to another embodiment of the present invention, there is provided an implantable medical device including the prosthetic implant.

The term "controlled release" as used herein refers to the release of NO or other bioactive compounds capable of immediately producing NO under in vivo conditions from an NO donor, a prosthetic implant or a surface of an implantable medical device at a predetermined rate. Controlled release implies that NO or the bioactive compounds do not come off the donor, the prosthetic implant or the surface of the implantable medical device in an unpredictable, sporadic fashion or as a burst upon contact with a certain biological environment. However, an exception to the above definition is abrupt releases predetermined by design, such as those occurring when the bioactive compound included in a thermosensitive hydrogel is directly exposed to in vivo conditions upon decompostion of a thermosensitive hydrogel below the phase transition temperature. In certain embodiments of the donor for controlled release of NO or the above-described bioactive compounds, it may be favorable to have a burst release at an initial stage in which the prosthetic implant or the implantable medical device is installed, followed by a gradual release thereafter. The release rate may be maintained at a steady state (referred to as "timed release" or zeroth order kinetics), that is, an even release of a certain amount of NO over a predetermined time (with or without an initial burst release) or it may be a gradient release. The gradient release implies that the concentration of NO or bioactive compounds released from the prosthetic implant or the surface of the implantable medical device changes over time. The lifetime of NO or the bioactive compound capable of immediately producing NO is very short when directly exposed to the biological environment. Thus, if the NO donor in the form of a hydrogel is capable of delaying the release of NO molecules or bioactive compound molecules, this pertains to the controlled release defined herein.

The term "hydrogel" as used herein refers to a semi-solid network in which organic molecules other than small molecules are suspended in an aqueous dispersion medium. The organic molecules in a hydrgel form a water-insoluble network in which physical crosslinks are formed between them. The term "thermosensitive hydrogel" as used herein indicates those where the organic molecules to form the hydrogel exist in a fluid form such as a solution, or a sol in an aqueous dispersion medium below room temperature, but undergo a phase transition upon a temperature increase into a certain range of temperature above the critical temperature, thereby forming a hydrogel without chemical cross-links. Depending on the type of the constitutive organic molecules, a thermosensitive hydrogel may exhibit such behavior as a sol (or another type of fluid)-gel transition or, in a more complex fashion, a sol (or another type of fluid)-gel-sol (or another type of fluid) transition upon a temperature increase. The sol-gel interconversion of a thermosensitive hydrogel may be particularly affected by pH and the concentration of the organic molecules.

The term "copolymer" as used herein refers to, unless otherwise particularly indicated herein, any type of copolymers, such as a linear copolymer, a random copolymer, a block copolymer, a graft copolymer, a star copolymer, and the like. In addition, unless otherwise indicated herein, the repetition number and type of the monomers or repeating units constituting the copolymer are not particularly limited. For example, when one denotes an ethylene glycol-derived repeating unit and a propylene glycol-derived repeating unit respectively as EG and PG for an ethylene glycol/propylene glycol copolymer, it is meant herein that this copolymer includes not only a random copolymer having the average composition of $(EG)_m(PG)_n$, but also a diblock copolymer of the composition $(EG)_m(PG)_n$, and a triblock copolymer of the composition $(EG)_l(PG)_m(EG)_n$, or the like. In addition, when one denotes a lactate(or lactide)-derived repeating unit and a glycolate (or glycolide)-derived repeated unit respectively as L and G for a lactate-glycolate-ethylene glycol copolymer, it is meant herein that this copolymer includes not only a triblock copolymer having the average composition of $(G)_l(EG)_m(L)_n$, but also such triblock copolymers as those with the composition $(EG)_l(G/L)_m(EG)_n$, where a mixed G/L block with both G and L repeating units and an ethylene glycol block coexist. In the formulae above, l, m, and n are positive numbers.

The term "prosthetic implant" or "implant" as used herein refers to any type of articles that can be placed at a position allowing the articles to exhibit physiological effects in the body of an animal including humans and mammals by releasing NO and capable of being equipped with a donor for controlled release of NO on its surface. In this regard, the entirety of the implant need not be inserted into the human or animal body as long as a portion of it is placed therewithin. For example, connection parts such as tubes and wires may exist outside the human body. The term "implantable medical device" or "medical device" as used herein is equivalent to the term "prosthetic implant", and encompasses medical devices for treatment, medical procedure, operation, diagnosis, and examination. The implantable medical device may also be entirely or partially inserted into the human body for a predetermined period of time. For example, only a probe or a sensor of the implantable medical device is inserted thereinto.

The inventive donor for controlled release of NO is a polymer comprising a main chain and a side chain that is linked to the main chain by a chemical bond. This chemical bond is generally a covalent bond, but is not limited thereto. For example, non-covalent intermolecular force such as biotin-avidin interaction that has strength comparable to covalent bonds may serve as the chemical bond linking the main and side chains. At its side chain or as part of its main carbon backbone, the donor has a diazeniumdiolate functional group capable of releasing NO when exposed to the biological environment.

The donor has a diazeniumdiolate functional group linked thereto by a chemical bond, and exists in a fluid state such as a sol, an emulsion, a dispersion, or a liquid below room temperature while it undergoes a phase transition upon contact with the body environment, e.g., a general pH and temperature in the human body, thereby forming a hydrogel. Thus, the controlled release donor of the present invention, a polymer capable of forming a thermosensitive hydrogel, conveniently supports the so-called in situ gel formation where the donor is inserted in a liquid state into a desired site of the body.

A gel is a porous elastic solid having condensed properties of a solid and diffusive transport properties of a liquid. The gel properties are greatly desired in the controlled release of an active material. A hydrogel has similar properties to those of natural biological soft tissues and is highly compatible with the biological soft tissues, and thus is used in the prosthetic implant. A desired concentration of the donor having the functional group capable of releasing NO may be easily coated on a surface of the prosthetic implant or the implantable medical device to a desired thickness. When the prosthetic implant or the implantable medical device is inserted into the human body, the donor of the present invention harbored in this implant or device exists as a hydrogel and thus allows highly labile, unstable NO to be slowly released without a sudden burst.

In the donor, the carbon backbone of its main chain plays a key role in the formation of a hydrogel. Preferably, the polymers constituting the main chain of the NO donor of the present invention form a thermosensitive hydrogel regardless whether they are linked to the side chain or they exist as independent polymers unlinked to the side chain. A partial list of examples of the polymers constituting the carbon backbone of the main chain of the donor may include an ethylene glycol/propylene glycol copolymer, a lactate/glycolate copolymer, a lactate/ethylene glycol copolymer, a lactate-glycolate-ethylene glycol copolymer, a lactate-glycolate-propylene glycol-ethylene glycol copolymer, an ε-caprolactone/ethylene glycol copolymer, a 3-hydroxybutyrate/propylene glycol copolymer, a propylene fumarate/ethylene glycol copolymer, an organophosphagen/ethylene glycol copolymer, a polypeptide-based block copolymer, and a copolymer including at least two of these copolymers linked to one another. The carbon backbone of the main chain of the donor may be a biodegradable polymer. In addition, the carbon backbone of the main chain of the donor may be a polymer obtained by attaching a repeating unit having a functional group (e.g., an ester functional group) for accelerating or inducing biodegradation to a non-biodegradable polymer or a conjugate of biomolecules, such as saccharide. The donor having, as a carbon backbone of the main chain, the polymer or the conjugate of biomolecules, may also form a thermosensitive hydrogel. In this regard, it will be obvious to one of ordinary skill in the art that the non-biodegradable polymer may be selected from the group consisting of the above-described copolymers.

In particular, the carbon backbone of the main chain of the donor may be a block copolymer. For example, the block copolymer may be an A-B-A type block copolymer. As a polymer capable of forming a thermosensitive hydrogel, more complicated block copolymers than the A-B-A type block copolymer are known.

The A-B-A type block copolymer capable of forming a hydrogel has both a hydrophilic block or segment and a hydrophobic block or segment. As the temperature increases, a thermosensitive polymer for forming a hydrogel reversibly forms a hydrogel or the hydrogel is dissociated into the polymer according to the temperature since most of the thermosensitive polymers do not include chemical cross-links. The driving force for forming a hydrogel at high temperatures is the increase in hydrophobic interaction that accompanies the temperature increase. Such polymers are mostly self-assembled to form physical cross-links.

Organic polymers capable of forming a hydrogel are well known in the art, and thus a detailed description thereof is not provided herein. A polymer that undergoes phase transition at an appropriate temperature and is maintained in a hydrogel state in an appropriate temperature range, according to the use of the donor may be selected by one of ordinary skill in the art from the group of the above-described copolymers, and a hydrogel may be formed by one of ordinary skill in the art by modifying the polymer, if necessary.

The block copolymer used in the main chain of the donor may be a triblock copolymer, for example, a polyethylene glycol-polypropylene glycol-polyethylene glycol (PEG-PPG-PEG) copolymer. As a commercially available triblock copolymer, pluronic F127 (Product name) manufactured by BASF, Germany may be used, and an average composition thereof is $(EG)_{99}\text{-}(PG)_{65}\text{-}(EG)_{99}$ (molecular weight: 12,600).

The pluronic F127 is a biocompatible, bioabsorbable polymer approved by the Food and Drug Administration (FDA) in the U.S. for use on humans.

In particular, the main chain of the donor may be the above-described PEG-PPG-PEG copolymer having a molecular weight in a range of about 4,600 to about 12,600.

The side chain of the donor is a polymer linked to the main chain by a chemical bond, and the donor includes a diazeniumdiolate functional group capable of generating and releasing NO at a portion of a backbone of the polymer side chain or as a side chain functional group.

NO is highly labile, particularly when light, heat and humidity conditions are beyond optimal conditions. The main chain of the donor for controlled release of NO plays a key role in formation of a hydrogel, and thus it is difficult for the donor to include a functional group capable of producing NO at its main chain. Thus, a side chain of the donor which has an appropriate length, thus not obstructing the formation of the hydrogel, and has a functional group capable of producing and releasing NO may be linked to the main chain of the donor by a chemical bond, whereby a release time of NO in the body may be increased.

The diazeniumdiolate functional group at the side chain of the donor may also be referred to as NONOate and may be represented by the formula of RR'N—N(O)=NO—. A diazeniumdiolate compound may be stably stored in a solid state and has a high solubility with respect to water, and a release pattern such as a release rate or method may be adjusted according to a structure of the remaining portion of the donor other than the side chain thereof to which the NONOate functional group is linked. In addition, the diazeniumdiolate compound is biodegradable at normal body temperatures and pH and can be released in various patterns according to the pH. The donor including the diazeniumdiolate functional group can release a relatively high concentration of NO since two NO molecules are released per diazeniumdiolate functional group.

Diazeniumdiolate may be obtained, as illustrated in Formula 1 below, by reacting secondary amine with NO.

<Formula 1> secondary amine    diazeniumdiolate (NONOate)

The side chain having the diazeniumdiolate functional group may be prepared using various methods. For example, a chain including a secondary amine nitrogen in the backbone thereof (in other words, where $R^1$—N—$R^2$ in Formula 1 above is linked within the backbone along the main longitudinal direction of the corresponding side chain) may be used as the side chain of the donor. Alternatively, the side chain of the donor may be prepared using an oligopolymer including secondary amine nitrogen at a side chain thereof.

Alternatively, diazeniumdiolate may be obtained by linking such a secondary amine nitrogen-containing oligopolymer to a main chain by a chemical bond and reacting an organic polymer with the oligopolymer linked thereto with NO.

The NO-releasing properties of diazeniumdiolates may be controlled by modifying functional groups corresponding to $R^1$ and $R^2$ in Formula 1. As depicted in Formula 1, since diazeniumdiolates have oxygen atoms with high electron density, active materials other than NO may be included in the side chain of the donor in the form of a conjugate in which other pharmaceutically active materials are linked to the oxygen atoms of diazeniumdiolate.

In an embodiment of the present invention, the carbon backbone of the side chain of the donor may be selected from secondary amine-containing polymers, for example, polypropyleneamine, polylysine, and the like and biopolymers such as chitosan. In a more particular embodiment, the carbon backbone of the side chain of the donor may be polyethyleneimine, for example, a branched polyethyleneimine (bPEI). In a particular embodiment of the present invention, the side chain of the donor (supposing that the side chain exists independent from the main chain) may be a PEI polymer having a molecular weight of 25,000 or less. When the molecular weight of the side chain of the donor is within this range, the toxicity of the donor in body cells can be prevented. In particular, the molecular weight of the PEI polymer may be 12,000 or less.

In another embodiment, the branched polyethyleneimine includes a side chain residue for forming chemical bonds to the backbone of the main chain at a branched portion. In particular, the side chain residue may be primary alkyleneamine. The alkyleneamine is linked to the nitrogen atom constituting a part of the chain backbone of bPEI via a carbon atom of the alkyleneamine. In this regard, the bPEI may preferably include both branched and unbranched ethyleneimine repeating units for solubility purposes.

In a particular embodiment of the present invention, the bPEI constituting the side chain of the donor may be a polymer represented by Formula 2 below.

<Formula 2> bPEI

The bPEI of Formula 2 may have a molecular weight of 25,000 or less, for example, a molecular weight of 12,000 or less. In this regard, a ratio of x to y is 1:2 in commercially available bPEI.

It is not particularly limited how much diazeniumdiolate functional group is introduced to bPEI constituting the side chain of the donor. A conversion rate of the secondary amine to diazeniumdiolate is generally 50% or greater, but is not limited thereto. Although it is often desirable to have the conversion rate of the diazeniumdiolate as high as possible, a skilled practitioner may appropriately increase or decrease the conversion rate by adjusting the conditions of the conversion reaction of the secondary amine to diazeniumdiolate depending on the desired NO-releasing properties of the final donor product to be obtained.

In a more particular embodiment of the present invention, the bPEI of Formula 2 may be used as an intermediate of the side chain of the donor, and a PEG-PPG-PEG copolymer may be used as an intermediate for the main chain of the donor. In this regard, the nitrogen of primary amine at the side chain residue of the branched polyethyleneimine may be linked via a carbamate linkage to the terminal oxygen of the triblock copolymer by using a chloroformate ester. The donor for controlled release of NO forms a hydrogel at normal body temperature and pH. In this regard, the temperature and pH conditions in the body may be appropriately adjusted by one of ordinary skill in the art, if necessary. For example, temperature and pH conditions in the human body are as follows: a critical temperature of a phase transition which induces a sol-to-gel phase transition upon a temperature rise is in a range of about 25 to about 35° C. and pH is in a range of about 5.5 to about 8.0.

In general, to form a hydrogel, a water dispersion solution including the donor is coated on a surface of a prosthetic implant or an implantable medical device. A phase transition temperature for a hydrogel may vary according to the concentration of the donor for controlled release of NO in water as a dispersion solvent. The dispersion concentration of the donor for coating may be appropriately determined by one of ordinary skill in the art corresponding to desired mechanical and chemical properties of a hydrogel and a release rate of NO. Although it is difficult to determine appropriate dispersion concentrations of all the donor polymers, the appropriate dispersion concentration of the donor may vary according to a material used in the donor and may be in a range of about 10 to about 30%. For example, an amount of a NO donor consisting of, as a main chain, polyethylene glycol-polypropylene glycol and, as a side chain, bPEI having an ethyleneamine side chain may be in a range of about 15 to about 25 wt % based on the total weight of a donor dispersion solution.

The donor may further include a pharmaceutically active material, in addition to NO. The pharmaceutically active material may be immobilized on the donor in the form of a conjugate linked to the donor by a chemical bond, or may be dispersed in the hydrogel without a chemical bond. The pharmaceutically active material may be covalently immobilized to oxygen atoms of the diazeniumdiolate functional group of the side chain of the donor. For example, an appropriate immobilization method of the pharmaceutically active material may be O-alkylation. For example, a positively charged pharmaceutically active material or a derivative thereof may be electrically bound to a negative charge of diazeniumdiolate. The pharmaceutically active material may be included in a dispersion solvent (water or aqueous solution) that disperses the donor, thereby being slowly released after the hydrogel is formed.

Examples of the pharmaceutically active material may include, but are not limited to, a thrombus formation-preventing agent, an anticoagulant, an antioxidant, an anti-inflammatory agent, and a wound healing enhancer. These pharmaceutically active materials are desirably used in the donor that may be used as a NO-releasing stent since they exhibit synergy effects. In particular, the pharmaceutically active materials include a vascular endothelial growth factor (VEGF), an anti-inflammatory agent, vitamin C, acetylsalicylate, a cholesterol-lowering drug, a thrombolytic agent, an antithrombotic agent, heparin, anticancer drugs, and oligonucleotides with anti-proliferative activity.

According to another embodiment of the present invention, there is provided a prosthetic implant and an implantable medical device whose surface is coated with the donor for controlled release of NO.

The prosthetic implant or the implantable medical device may be used both in a case where the controlled release of NO assists in improving original effects of the prosthetic implant or the implantable medical device and in a case for the purpose of only releasing NO or NO and an additional pharmaceutically active material. In particular, NO is used to relax vascular smooth muscles, promote wound healing, and regulate neurotransmission. Also, NO has sterilizing and antiviral effects. In particular, NO has an excellent antiviral effect against human papillomavirus (hPV).

In addition, the donor may assist the function of a chemical sensor that contacts blood or may itself function as a part of the chemical sensor that measures the concentration of NO. In this case, a main chain-side chain polymer including a side chain not having the diazeniumdiolate functional group and including secondary amine may be coated on a surface of the prosthetic implant or the implantable medical device. When NO generated in the human body permeates into a formed hydrogel, it reacts with the secondary amine in the main chain-side chain polymer, thereby generating diazeniumdiolate. In this regard, the donor may quantitatively measure the amount of the generated diazeniumdiolate, acting as a chemical sensor. Examples of the prosthetic implant or the implantable medical device may include a stent, a catheter, a subcutaneous implant, a chemical sensor, a lead, a pacemaker, a vascular graft, a dressing for a wound, a penile implant, an implantable pulse generator (IPG), an implantable cardiac defibrillator, and a nerve stimulator.

The coating of the donor for controlled release of NO on the surface of the prosthetic implant or the implantable medical device may be performed using well-known methods in the art. These methods may be appropriately selected by one of ordinary skill in the art according to the use of the donor and a detailed description thereof is not provided herein. For example, the coating process may be performed by immersing the prosthetic implant or the implantable medical device in a solution including the donor. Alternatively, the coating process may be performed by surface treating the prosthetic implant or the implantable medical device with the donor.

EXAMPLES

One or more embodiments of the present invention will now be described in greater detail with reference to the following examples. However, these examples are for illustrative purposes only and are not intended to limit the scope of the invention.

Example 1

Branched Polyethyleneimine Including Diazeniumdiolate Functional Group (bPEI-NONOate)

Each of 0.5 g portions of three branched polyethyleneimine (bPEI) copolymers (available from Polysciences, USA, the ratio of primary to secondary to tertiary amine groups is 25:50:25), each of the copolymers having weight average molecular weights of 600, 10,000, and 25,000, respectively, and having a repeating unit of a primary amine side chain and a repeating unit of ethyleneimine, was put in a 100 ml beaker and 10 ml of methanol and 20 ml of tetrahydrofuran (THF) were added to each beaker, and each resultant mixture was stirred for 30 minutes.

Figure 1:
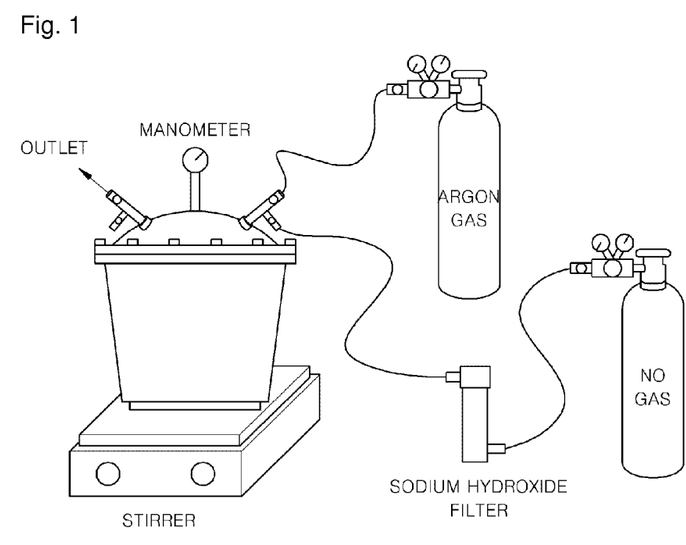
FIG. 1 is a schematic diagram illustrating a reactor used for synthesizing a diazeniumdiolate functional group of the side chain that constitutes the nitric monoxide (NO) donor according to an embodiment of the present invention.

0.63 g (the amount equivalent to the total combined amounts of primary to tertiary amine groups of each bPEI) of sodium methoxide (NaOMe) was dissolved in 10 ml of methanol, and the mixture was put in each of the beakers containing the bPEIs. The beakers were placed in a reactor and the inside of the reactor was purged twice with 20 psi of argon gas. Subsequently, 80 psi of NO was added to the reactor and it was left for 3 days to produce the bPEI-NON- Oates. The reactor used for the reaction is illustrated in FIG. 1. The produced bPEI-NONOates were separated by precipitating with diethyl ether.

The process of producing bPEI-NONOate is illustrated in Formula 3 below. In Formula 3, some secondary amine repeating units (the number of the repeating units is y) react with NO under a base to be converted to diazeniumdiolate functional groups (the number of the repeating units is z) but some do not react and remain as secondary amines (the number of the repeating units is w).

<Formula 3>

$y = w + z$

Analysis of Properties of Produced bPEI-NONOate

1) Confirm Formation of Diazeniumdiolate Functional Group

Figure 2:
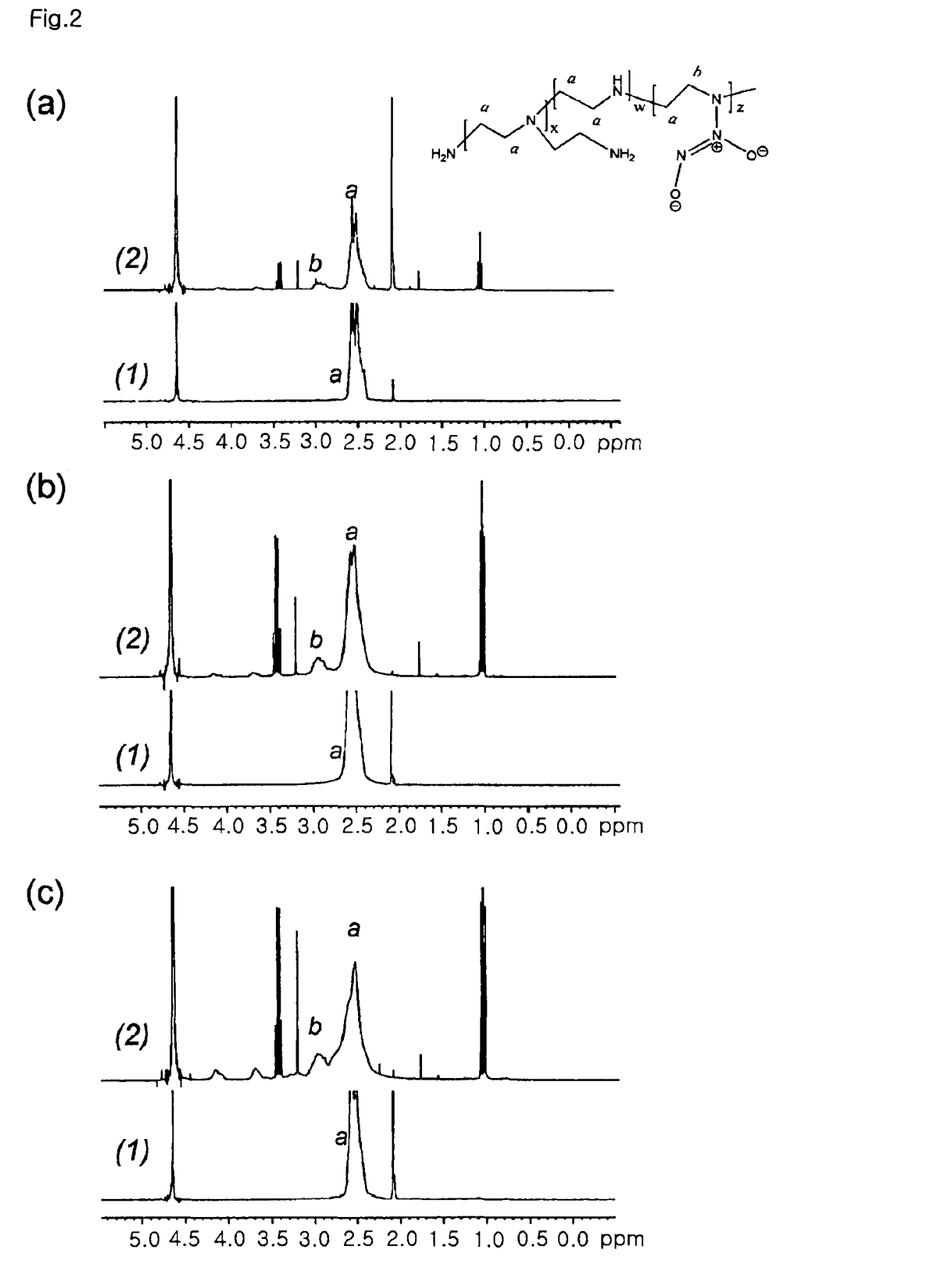
FIG. 2 illustrates the $^1$H-NMR spectrum of a diazeniumdiolate functional group-containing side chain according to one embodiment.

It was determined by quantitative measurement via nuclear magnetic resonance (NMR) whether each produced bPEI-NONOate has a diazeniumdiolate functional group. FIG. 2 illustrates $^1$H-NMR spectrum results of the reaction product. Although the α-hydrogen (corresponding to position a in FIG. 2) of the tertiary amine in bPEI molecules of Formula 3 appears at δ=2.6 ppm in $^1$H-NMR spectrum, once the diazeniumdiolate functional group is formed, this former α-hydrogen of the tertiary amine now appears at δ=3.1 ppm in the $^1$H-NMR spectrum (corresponding to position b in FIG. 2). As illustrated in FIG. 2, as a result of NMR spectrum analysis of the product, it was confirmed that of the secondary amines in the bPEI copolymers, 15.3% was converted to diazeniumdiolate for the bPEI having a molecular weight of 600 (bPEI600) (refer to FIG. 2A), 13.8% for the bPEI having a molecular weight of 10,000 (bPEI10K) (refer to FIG. 2B), and 16.0% for the bPEI having a molecular weight of 25,000 (bPEI25K) (refer to FIG. 2C). Hereinafter, the diazeniumdiolate of the bPEI with a molecular weight of 600 confirmed by the $^1$H-NMR spectrum of FIG. 2A is referred to as bPEI600-NONOate, the diazeniumdiolate of the bPEI with a molecular weight of 10,000 confirmed by the $^1$H-NMR spectrum of FIG. 2B is referred to as bPEI10K-NONOate, and the diazeniumdiolate of the bPEI with a molecular weight of 25,000 confirmed by the $^1$H-NMR spectrum of FIG. 2C is referred to as bPEI25K-NONOate.

1) Spectroscopic Analysis of Diazeniumdiolate

Figure 3:
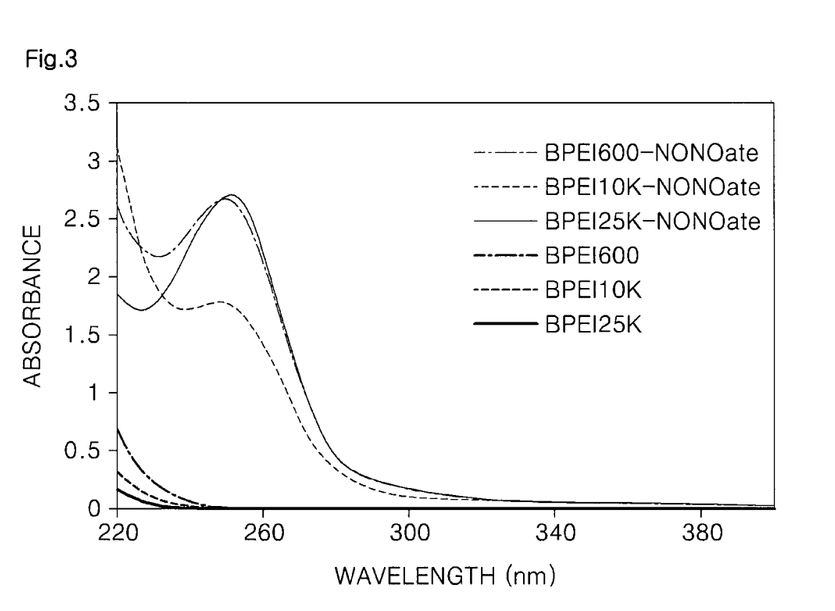
FIG. 3 is a graph showing ultraviolet (UV) spectrum of a diazeniumdiolate functional group-containing side chain according to one embodiment.

When ultraviolet (UV) absorption spectroscopy is performed on the diazeniumdiolate functional group produced from the secondary amine group of bPEI, an absorption peak generally appears at 250 to 260 nm. FIG. 3 is a graph showing UV spectrum measurement results of synthesized bPEI-NONOates at 200 to 400 nm. In FIG. 3, bPEI600, bPEI10K, and bPEI25K respectively indicate bPEIs having molecular weights of 600, 10,000, and 25,000 prior to the reaction, and bPEI600-NO, bPEI10K-NO, and bPEI25K-NO respectively indicate their corresponding diazenium-diolates. As illustrated in FIG. 3, as a result of UV absorption spectroscopy, it is confirmed that the absorption peaks of bPEI600-NO, bPEI10K-NO, and bPEI25K-NO appear at 250 to 260 nm unlike the bPEIs prior to the reaction.

3) Analysis of NO Release

The analysis of NO release was performed using a general detection method, e.g., Griess analysis (refer to H. H. H. W. Schmidt and M. Kelm, in *Methods in Nitric Oxide Research*, ed. M. Feelish and J. S. Stamler, Wiley & Sons, New York, 1996.). Highly labile NO reacts with oxygen or moisture in a reaction solvent to produce nitrogen dioxide, the nitrogen dioxide reacts with sulfanilamide to be activated, and the activated resultant material reacts with naphthylene diamine to produce an azo compound that absorbs light with a wavelength of 548 nm.

Figure 4:
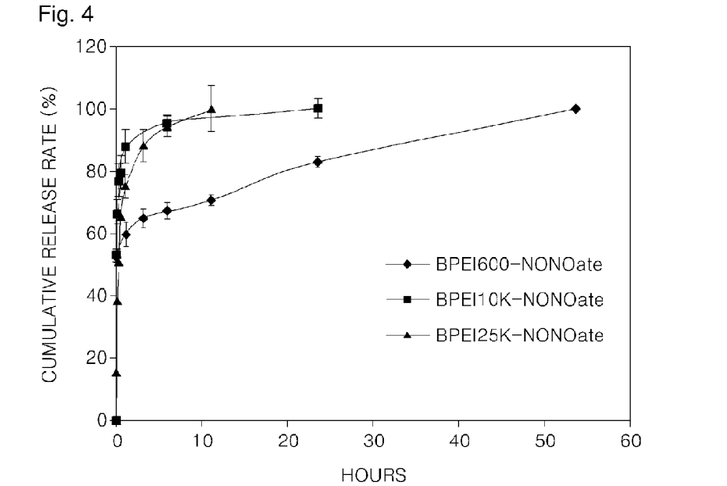
FIG. 4 is a graph showing the NO-releasing properties of a diazeniumdiolate functional group-containing side chain according to one embodiment.

The results of analyzing the three synthesized bPEI-NONOates by using such a principle are illustrated in FIG. 4. Abbreviated compound names shown in FIG. 4 are the same as defined in the description with regards to FIG. 3. Although the NO release profile did not exhibit any distinct difference in terms of the molecular weight of bPEI-NONOate, bPEI10K-NONOate had the largest initial release amount, the fastest release rate among the three bPEI-NONOates, and it released NO for about 24 hours. The initial release amount of bPEI25K-NONOate was second largest and the NO release lasted for about 11 hours. The initial release amount of bPEI600-NONOate was the smallest and bPEI600-NONOate slowly released NO for the longest period of time (54 hours). Thus, subsequent experiments were performed using bPEI600-NONOate.

Example 2

Main Chain-side Chain Construct not Including Diazeniumdiolate Functional Group (1) Synthesis of F127-bPEI 10.0 g of Pluronic F127 (registered trademark by BASF) having a molecular weight of 12,600 was put into a 250 ml round-bottom flask and dissolved in 70 ml of methylene chloride. The flask was then purged with nitrogen. Subsequently, 1.29 g of p-Nitrophenyl chloroformate (p-NPC) was dissolved in 70 ml of methylene chloride and the mixed solution was put into a dropping funnel. While the Pluronic F127 solution was being stirred in the nitrogen atmosphere, p-NPC was dropped to the flask to incur a reaction therebetween for 12 hours, thereby obtaining an end-activated Pluronic F127. The resultant product was separated using diethylether precipitation. Subsequently, the end-activated Pluronic F127 was reacted with bPEI to link bPEI to an end terminal thereof. The Synthesis Scheme of F127-bPEI is illustrated in Formula 4. In Formula 4, F127-bPEI denotes Pluronic F127 with bPEI linked to the end terminal thereof.

<Formula 4>

In more detail, the above-described end activated Pluronic F127 was reacted with an excess amount of bPEI600 at equivalent weight ratios of 1:1.5, 1:3, and 1:10 to respectively produce three main chain-side chain constructs not including a diazeniumdiolate functional group (F127-bPEI0.8, F127-bPEI1.0, and F127-bPEI1.3, respectively).

F127-bPEI0.8 was synthesized as follows: 43 mg of bPEI600 (1.5 equiv.) was put into a 100 ml round-bottom flask and then dissolved in 20 ml of methylene chloride and 1 ml of triethyleneamine. The flask was then purged with nitrogen. 0.6 g of the end-activated Pluronic F127 (1 equiv.) was dissolved in 20 ml of methylene chloride and the resultant mixture was put into a dropping funnel. While the resultant mixture including bPEI was stirred in the nitrogen atmosphere in an ice bath, the end-activated Pluronic F127 was dropped to the flask to incur a reaction therebetween for 12 hours to obtain F127-bPEI0.8. The synthesized F127-bPEI0.8 was dialyzed with MWCO dialysis 10000 as a dialysis membrane for separation to remove impurities therefrom and then freeze-dried to obtain a final product. F127-bPEI1.0 and F127-bPEI1.3 were respectively synthesized using the same method as used in the synthesis of F127-bPEI0.8, except that 86 mg of bPEI600 (3 equiv.) and 0.6 g of the end-activated Pluronic F127 (1 equiv.) were used, and 289 mg of bPEI600 (10 equiv.) and 0.6 g of the end-activated Pluronic F127 (1 equiv.) were used.

Figure 5:
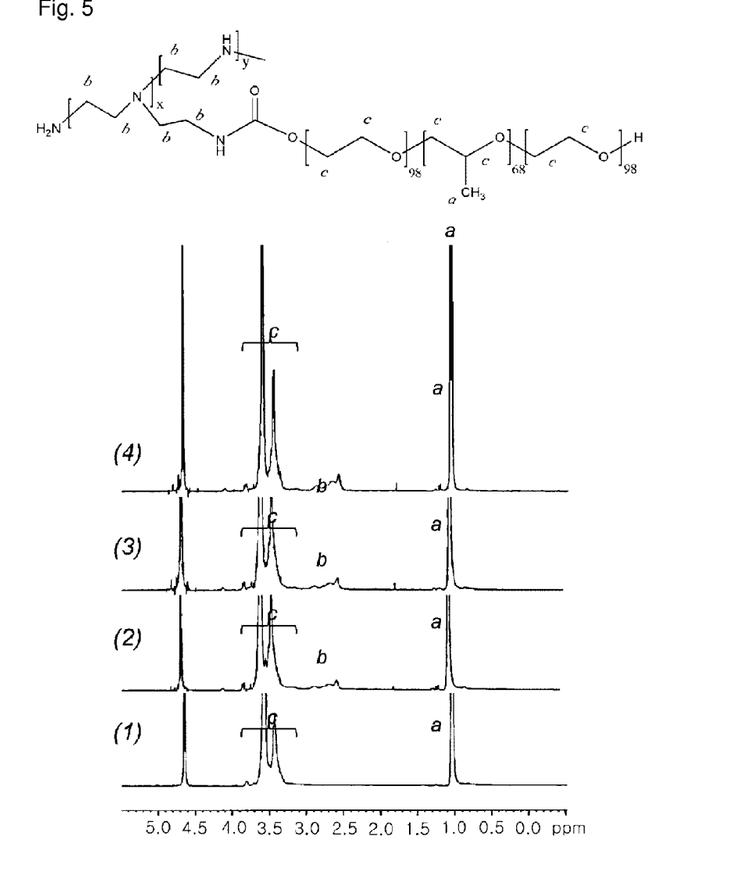
FIG. 5 illustrates the $^1$H-NMR spectrum of a main chain-side chain construct free of diazeniumdiolate functional group.

Analysis of Properties of Produced F127-bPEI (1) Confirm Binding Between Pluronic F127 and bPEI It was determined by quantitative measurement via $^1$H-NMR whether Pluronic F127 and bPEI in the three produced main chain-side chain constructs were linked via a carbamate linkage. $^1$H-NMR spectra results of the three produced main chain-side chain constructs are illustrated in FIG. 5. In general, as represented by a and c in FIG. 5, $^1$H-NMR the spectrum of Pluronic F127 is largely divided into methyl hydrogens a and methylene hydrogens c. The $^1$H-NMR signal of the methyl hydrogen a of a propylene glycol-derived repeating unit appears at δ=1.15 ppm while the $^1$H-NMR signal of the remaining methylene hydrogen c appears at δ=3.2 to 4.0 ppm. In addition, the $^1$H-NMR signal of carbon-linked hydrogen b of bPEI appears at δ=2.6 ppm. In FIG. 5, (1), (2), (3), and (4) respectively indicate $^1$H-NMR spectra of unreacted Pluronic F127, the produced F127-bPEI0.8, the produced F127-bPEI1.0, and the produced F127-bPEI1.3. From the results of FIG. 1, it was confirmed that for F127-bPEI0.8, 40% of the terminal hydroxyl groups of the main chain of Pluronic F127 was bound to bPEI, 50.0% for F127-bPEI1.0, and 62.5% for F127-bPEI1.3.

2) Confirmation of Gel Formation

Figure 6:
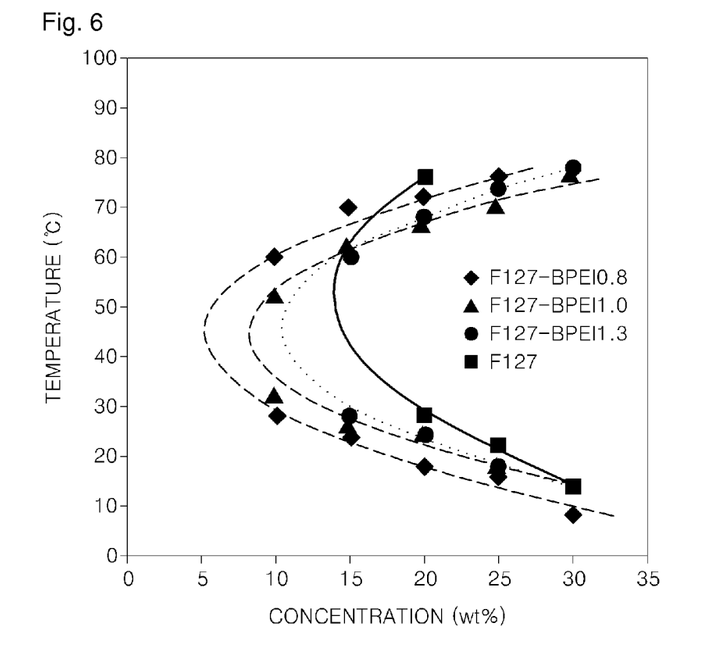
FIG. 6 is a graph analyzing the gelation properties of a main chain-side chain construct free of diazeniumdiolate functional group in terms of temperature and concentration.

A gelation experiment was performed to confirm whether the main chain-side chain construct consisting of Pluronic F127 and bPEI is capable of forming a thermosensitive hydrogel like Pluronic F127 and if so, how it affects gelation properties. A sol-gel presence according to temperature and concentration (inverted gelation test) was recorded in such a manner that if there was a flow of a solution when main chain-side chain constructs dispersed in water at various concentrations (wt %) were inverted, it was determined as a solution (sol) state and if not, it was determined as a gel state. The test results are illustrated in FIG. 6. All the produced main chain-side chain constructs were capable of forming a thermosensitive hydrogel even a much lower concentration than that of Pluronic F127. In terms of stability, F127-bPEI0.8, F127-bPEI1.0, and F127-bPEI1.3 formed stable hydrogels in this order. Thus, all the three constructs serve as a suitable precursor for use in preparing a donor.

Example 3

Diazeniumdiolate Functional Group-containing Donor F127-bPEI-NONOate (1) Synthesis of F127-bPEI-NONOate 0.46 g of F127-bPEI was put into a 100 ml beaker and 0.23 ml of 5.3 M sodium methoxide, 2.07 ml of methanol, and 2.3 ml of tetrahydrofuran were added thereto. The beaker was placed in a reaction container as illustrated in FIG. 1 and air in the reaction container was exhausted twice with 20 psi of argon. Subsequently, 80 psi of nitric monoxide was added to the container and the container was maintained for 3 days. The reaction product was precipitated with diethylether to be separated. The reaction scheme is illustrated in Formula 5 below.

<Formula 5>

F127-bPEI

F127-bPEI-NONOate

Confirmation of Properties of F127-bPEI-NONOate

1) Confirm Whether Diazeniumdiolate Functional Group is Formed

Figure 7:
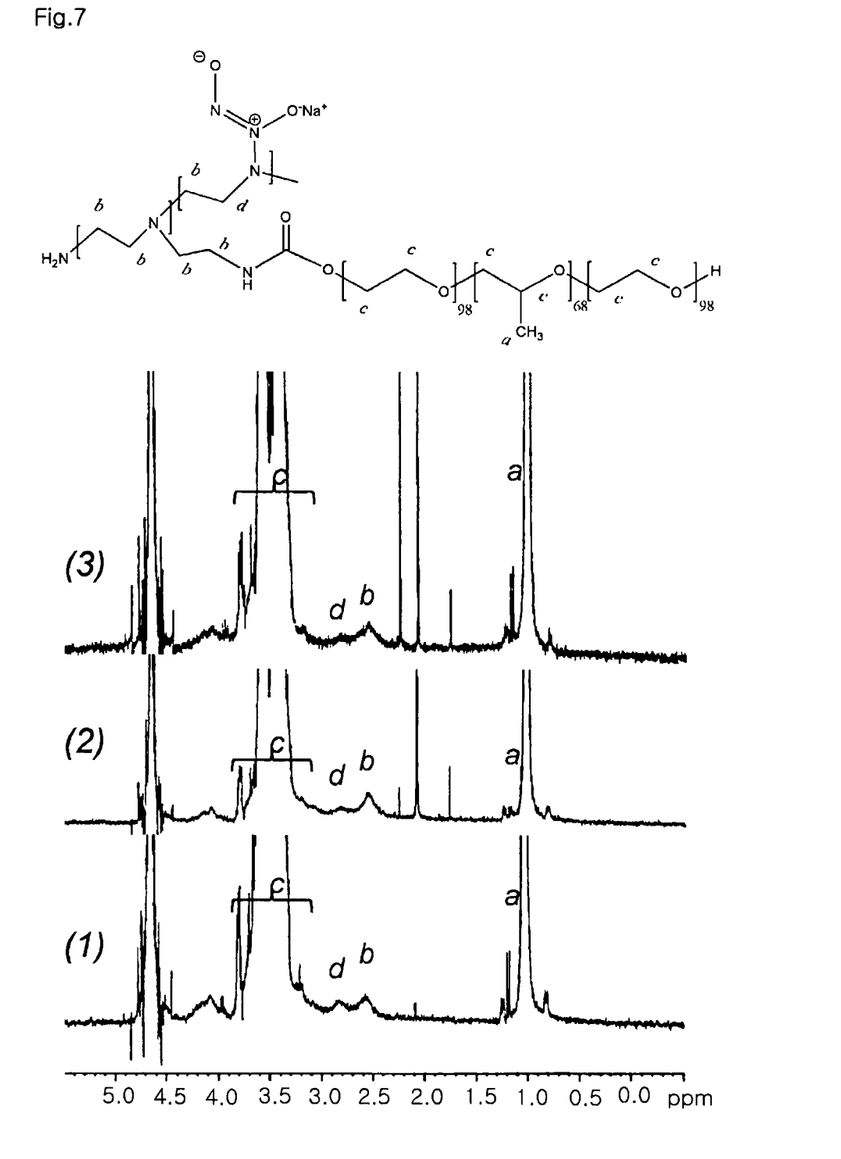
FIG. 7 illustrates the $^1$H-NMR spectrum of an NO donor according to an embodiment.

It was determined by quantitative measurement via NMR whether a diazeniumdiolate functional group is formed in F127-bPEI1.3-NONOate. The $^1$H-NMR spectrum results are illustrated in FIG. 7. F127-bPEI generally has its peaks at three positions in $^1$H-NMR spectrum. In the $^1$H-NMR spectrum, the peak for the methyl hydrogen (a of FIG. 7) of a propylene glycol-derived repeating unit of Pluronic F127 appears at $\delta=1.15$ ppm while the peak for methylene hydrogens (c of FIG. 7) appears at $\delta=3.2$ to 4.0 ppm. In addition, methylene hydrogens alpha (a of FIG. 7) to the diazeniumdiolate functional group of bPEI show peaks around $\delta=2.9$ ppm, while the peaks for methylene hydrogens (b of FIG. 7) of bPEI generally appear around $\delta=2.6$ ppm in the $^1$H-NMR spectrum.

In FIG. 7, (1), (2), and (3) respectively indicate the $^1$H-NMR spectra of produced F127-bPEI0.8-NONOate, produced F127-bPEI1.0-NONOate, and produced F127-bPEI1.3-NONOate. NMR analysis confirmed that in the course of preparing the donor, 35.1% of the secondary amine groups prior to the reaction in the main chain-side chain construct was converted to diazeniumdiolate functional groups for F127-bPEI0.8-NONOate, 33.1% for F127-bPEI1.0-NONOate, and 35.1% for F127-bPEI1.3-NONOate.

1) Hydrogel Formation Experiment

An experiment was performed on F127-bPEI-NONOate to confirm a formation of a thermosensitive hydrogel. As a result, F127-bPEI-NONOate was confirmed to form a similar hydrogel to that formed using F127-bPEI illustrated in FIG. 6 (data not shown). All the three above-described F127-bPEI-NONOates stably formed thermosensitive hydrogels as in F127-bPEI.

1) Analysis of NO Release

Figure 8:
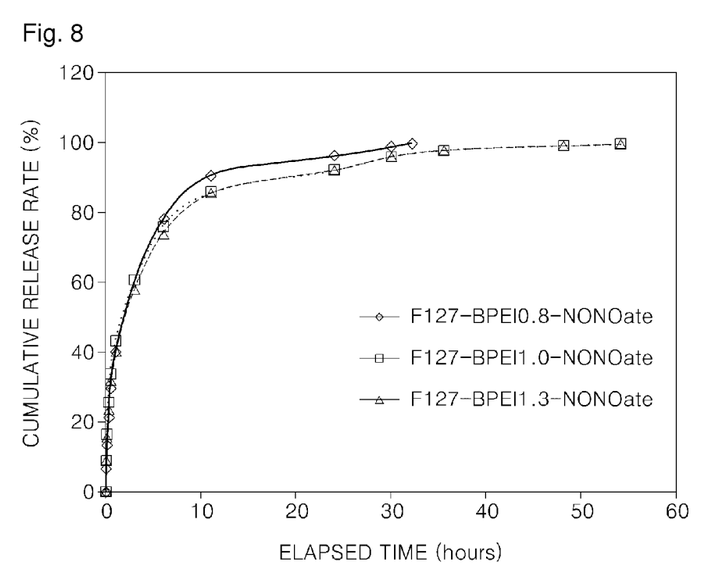
FIG. 8 is a graph showing the NO-releasing properties of an NO donor according to an embodiment.

NO release of the F127-bPEI-NONOate donors that formed hydrogels was analyzed by Griess analysis as in bPEI-NONOate. The analysis results are illustrated in FIG. 8. In bPEI600-NONOate, the half-life of total released NO was no more than 1 minute while the half-lives of total released NO of F127-bPEI0.8-NONOate, F127-bPEI1.0-NONOate and F127-bPEI1.3-NONOate were in a range of about 1.6 to 2.4 hours, which means that F127-bPEI0.8-NONOate, F127-bPEI1.0-NONOate and F127-bPEI1.3-NONOate released NO at no less than 100 times slower rate than bPEI600-NONOate.

1) Cell Toxicity Test

Figure 9:
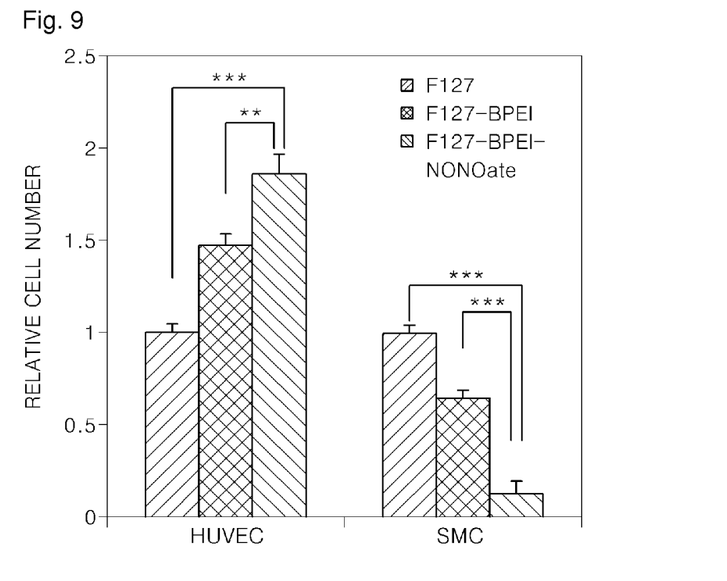
FIG. 9 is a graph showing that a gel formed of a donor for the controlled release of NO according to an embodiment of the present invention enhances the growth of vascular endothelial cells and inhibits the growth of vascular smooth muscle cells.

A cell toxicity test (analyzed by a CCK-8 kit available from Dojindo, Japan) was performed on F127-bPEI0.8-NONOate hydrogel. As the experimental groups, human umbilical vein endothelial cells (HUVECs), which are vascular endothelial cell lines, or coronary artery smooth muscle cells, which are vascular smooth muscle cell (SMC) lines, were cultured on a F127-bPEI0.8-NONOate hydrogel and the number of cultured cells was measured. As the control, the same cells as used in the experimental group were cultured on a general 24-well plate. The test results are illustrated in FIG. 9. The data in FIG. 9 is represented as a mean±standard deviation (n=3). Statistical analysis was done using the Student t test. The symbols  and * indicate statistical significance at levels of $p<0.001$ and $p<0.001$, respectively.

Referring to FIG. 9, F127-BPEI0.8-NONOate demonstrated 48.1% and 26.1% enhancement in the proliferation of HUVEC compared to those achieved by F127 and F127-BPEI0.8 mediated proliferation, respectively. Furthermore, the proliferation of SMC was significantly reduced by 35.0% and 80.8% on the F127-BPEI0.8-NONOates-coated plates compared to F127 and F127-BPEI0.8-coated plates, respectively.

From the results illustrated in FIG. 9, it was confirmed that the donor for controlled release of NO exhibited different physiological effects with respect to the HUVECs and the SMCs. Thus, when the donor is used in a stent among various applications, instent restenosis may be stably and efficiently prevented.

It should be understood that the exemplary embodiments described herein should be considered in a descriptive sense only and not for purposes of limitation. Descriptions of features or aspects within each embodiment should typically be considered as available for other similar features or aspects in other embodiments.

The invention claimed is:

1. A donor for controlled release of nitric oxide, wherein the donor comprises a polymer comprising:
    a main chain of organic polymer; and
    a side chain directly covalently linked to the main chain and having an N-bound diazeniumdiolate functional group,
    wherein the backbone of the main chain comprises a block copolymer selected from the group consisting of an ethylene glycol/propylene glycol copolymer, a lactate/glycolate copolymer, a lactate/ethylene glycol copolymer, a lactate-glycolate-ethylene glycol copolymer, a lactate-glycolate-propylene glycol-ethylene glycol copolymer, an ε-caprolactone/ethylene glycol copolymer, a 3-hydroxybutyrate/propylene glycol copolymer, a propylene fumarate/ethylene glycol copolymer, an organophosphagen/ethylene glycol copolymer, and a polypeptide-based block copolymer,
    wherein the backbone of the side chain comprises a polymer selected from the group consisting of polyethyleneimine, polypropyleneimine, polypeptide, and chitosan, and
    wherein the polymer of the donor undergoes a sol-to-gel phase transition upon a temperature rise, wherein the critical temperature of the phase transition is in the range of 25 to 35° C. and the polymer of the donor forms a hydrogel without chemical cross-links above the critical temperature and at an in vivo pH.

2. The donor of claim 1, wherein the backbone of the main chain comprises an ethylene glycol/propylene glycol copolymer.

3. The donor of claim 1, further comprising, in the hydrogel, at least one pharmaceutically active material selected from the group consisting of vascular endothelial growth factor (VEGF), anti-inflammatory agents, vitamin C, acetylsalicylate, cholesterol-lowering drugs, thrombolytic agents, antithrombotic agent, heparin, anticancer drugs and oligonucleotides with anti-proliferative activity.

4. The donor of claim 3, wherein the pharmaceutically active material is not covalently linked to the donor, but is dispersed in the hydrogel.

5. The donor of claim 3, wherein the pharmaceutically active material is a conjugate covalently linked to oxygen atoms of the diazeniumdiolate functional group.

6. A prosthetic implant coated with the donor for controlled release of nitric oxide of claim 1 on its surface.

7. The prosthetic implant of claim 6, wherein the prosthetic implant is selected from the group consisting of stents, catheters, leads, subcutaneous implants, chemical sensors, pacemakers, vascular grafts, dressing for wound, penile implants, implantable pulse generators (IPG), implantable cardiac defibrillators, and nerve stimulators.

\* \* \* \* \*